United States Patent
Czernichow et al.

(10) Patent No.: US 9,493,743 B2
(45) Date of Patent: Nov. 15, 2016

(54) PRODUCTION OF A HUMAN BETA CELL LINE FROM AN EARLY POST NATAL PANCREAS

(71) Applicants: SARL ENDOCELLS, Paris (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR)

(72) Inventors: Paul Czernichow, Paris (FR); Philippe Ravassard, Paris (FR); Raphael Scharfmann, Paris (FR)

(73) Assignees: UNIVERCELL BIOSOLUTIONS, Toulouse (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR)

(*) Notice: Subject to any disclaimer, the term of this patent is extended or adjusted under 35 U.S.C. 154(b) by 0 days.

(21) Appl. No.: 14/352,519

(22) PCT Filed: Oct. 18, 2012

(86) PCT No.: PCT/EP2012/070612
§ 371 (c)(1),
(2) Date: Apr. 17, 2014

(87) PCT Pub. No.: WO2013/057164
PCT Pub. Date: Apr. 25, 2013

(65) Prior Publication Data
US 2014/0302155 A1    Oct. 9, 2014

Related U.S. Application Data

(60) Provisional application No. 61/548,526, filed on Oct. 18, 2011.

(51) Int. Cl.
| | | |
|---|---|---|
| A61K 48/00 | (2006.01) | |
| C12N 5/071 | (2010.01) | |
| A01K 67/027 | (2006.01) | |
| C12N 5/09 | (2010.01) | |
| G01N 33/50 | (2006.01) | |
| G01N 33/569 | (2006.01) | |

(52) U.S. Cl.
CPC ......... *C12N 5/0676* (2013.01); *A01K 67/0271* (2013.01); *C12N 5/0677* (2013.01); *C12N 5/0693* (2013.01); *G01N 33/5023* (2013.01); *G01N 33/56966* (2013.01); *A01K 2207/12* (2013.01); *A01K 2227/105* (2013.01); *A01K 2267/025* (2013.01); *A01K 2267/0362* (2013.01); *C12N 2501/33* (2013.01); *C12N 2501/734* (2013.01); *C12N 2503/00* (2013.01); *C12N 2510/04* (2013.01)

(58) Field of Classification Search
None
See application file for complete search history.

(56) References Cited

U.S. PATENT DOCUMENTS

| | | | |
|---|---|---|---|
| 6,110,743 A * | 8/2000 | Levine et al. | 435/456 |
| 7,041,634 B2 * | 5/2006 | Weber et al. | 514/6.7 |
| 7,745,216 B2 * | 6/2010 | Pang et al. | 435/366 |
| 2005/0123521 A1 | 6/2005 | Zern et al. | |
| 2005/0193432 A1 * | 9/2005 | Kuperwasser et al. | 800/18 |

FOREIGN PATENT DOCUMENTS

WO    WO-2008/102000 A1    8/2008

OTHER PUBLICATIONS

Minami et al. J Diabetes Investig. Dec. 3, 2010;1(6):242-51.*
Levitt et al. Diabetologia 2011;54:572-82, Online Oct. 9, 2010.*
Meier et al. Diabetes 2008;57:1584-94.*
International Search Report for International Application No. PCT/EP2012/070612 dated Jan. 30, 2013.
Narushima et al., "A human beta-cell line for the transplantation therapy to control type-1 diabetes," Nature Biotechnology, Nature Publishing Group. New York, New York, US, vol. 23, No. 10, Oct. 2005, pp. 1274-1282, XP008073144.
Peck et al., "Pancreatic stem cells: building, blocks for a better surrogate islet to treat type-1 diabetes," Annals of medicine, Taylor & Frances A B, SE, vol. 33, No. 3, 2001, pp. 186-192, XP009006630.
Ravassard et al., "A genetically engineered human pancreatic beta cell line exhibiting glucose-inducible insulin secretion," Journal of Clinical Investigation, vol. 121, No. 9, Sep. 2011, pp. 3589-3597, XP002689806.

(Continued)

*Primary Examiner* — Janice Li
(74) *Attorney, Agent, or Firm* — Foley & Lardner LLP

(57) ABSTRACT

The present invention relates to a method for preparing commercial scale quantities of human functional beta cells and to the establishment of cell lines from non-foetal pancreatic tissues. It also relates to a method of diagnosis using beta cell tumors or cells derived thereof. The method comprises sub-transplantation procedure to enrich the graft in proliferating beta cells, allowing to generate human Beta cell lines. Such lines express, produce and secrete insulin upon glucose stimulation. They have a gene expression profile that resembles to adult beta cells. In addition, the human beta cell lines are able to normalize glycemia of diabetic mice when transplanted, demonstrating their insulin secretion capabilities.

13 Claims, 2 Drawing Sheets

(56) References Cited

OTHER PUBLICATIONS

Figure 1:
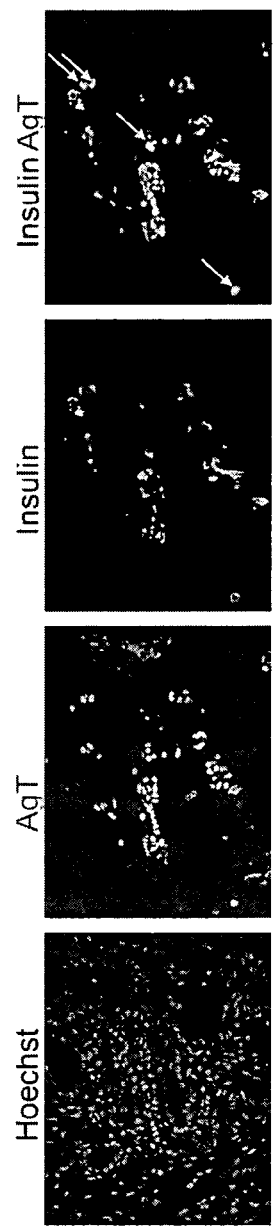

Ravassard et al., "A new strategy to generate functional insulin-producing cell lines by somatic gene transfer into pancreatic progenitors," PLOS ONE, vol. 4, No. 3, 2009, p. e4731, XP055048138.

Weir et al., "Finally! A human pancreatic beta cell line," Journal of Clinical Investigation, vol. 121, No. 9, Sep. 2011, pp. 3395-3397, XP002689807.

* cited by examiner

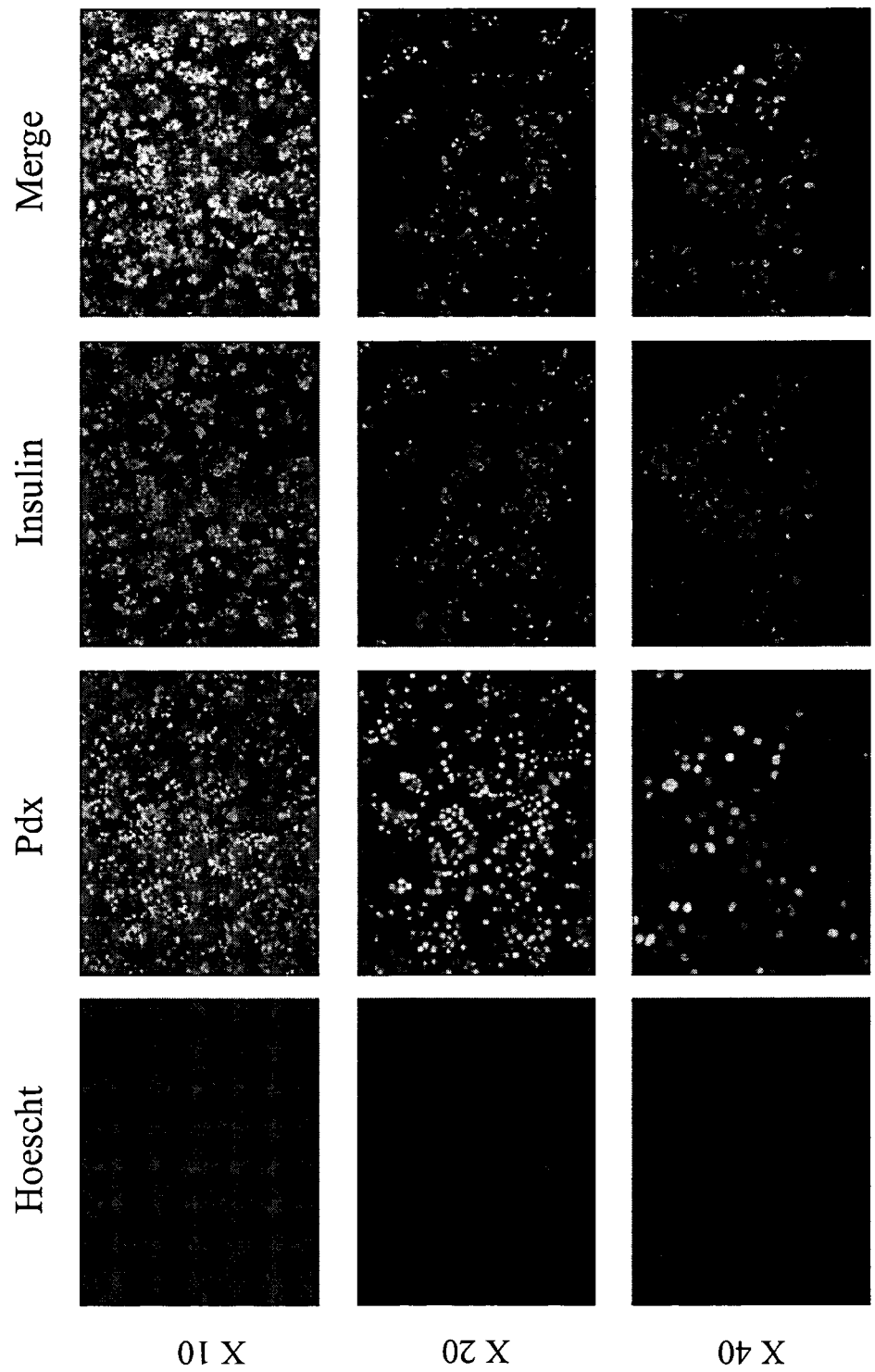

PRODUCTION OF A HUMAN BETA CELL LINE FROM AN EARLY POST NATAL PANCREAS

The present invention relates to a method for preparing human beta cells in vitro from pancreatic tissue. It particularly concerns obtaining insulin secreting cells from pancreas obtained during the early post natal period. It also relates to methods of diagnosis of diabetes using beta cell tumors or cells derived thereof.

BACKGROUND OF THE INVENTION

Diabetes is a chronic disease that afflicts 200 millions people worldwide. Type 1 diabetes results from autoimmune destruction of beta cells, while type 2 diabetes is caused by a combination of insulin resistance and inadequate insulin secretion. Thus, in both type 1 and type 2 diabetes, the functional beta cell mass is not sufficient to control glycemia.

The mature pancreas contains two types of tissue: exocrine tissue composed of acinar cells that produce enzymes (e.g., carboxypeptidase-A) secreted via the pancreatic ducts into the intestine and endocrine islets composed of cells that produce hormones such as insulin (beta cells), glucagon (alpha cells) somatostatin (delta cells) and pancreatic polypeptide (PP cells). Over the past decades research in the beta cell field profited from the establishment of insulin-secreting cell lines, such as RIN and INS1 cells derived from x-ray induced rat insulinoma (Asfari et al., 1992; Gazdar et al., 1980), HIT cells generated by transformation of hamster islet cells by SV40 (Santerre et al., 1981) and beta TC and Min6 cells derived from transgenic mice expressing SV40 T antigen under the control of the insulin promoter (Efrat et al., 1995; Efrat et al., 1993; Efrat et al., 1988; Hanahan, 1985; Knaack et al., 1994; Miyazaki et al., 1990). Such cell lines were useful for a better understanding of beta cell biology and could be used for drug screening.

Generation of pancreatic beta cells in large amount represents an important objective, because such beta cells could be used for cell therapy of diabetes. In addition, such pancreatic beta cells would also be useful for screening of new drugs that can modulate beta cell function. To this end, different approaches have been previously developed to generate pancreatic beta cells in large amount.

The first one consisted in using as starting material immature embryonic stem cells (ES cells) to produce mouse or human beta cells. The major advantage is that ES cells self-renew indefinitely in culture, and have the capacity to differentiate to multiple cell types, and thus to pancreatic beta cells. While quite a large amount of publications appeared during the past years on beta cells production from ES cells (Assady et al., 2001; Blyszczuk et al., 2003; Brolen et al., 2005; Hori et al., 2002; Lumelsky et al., 2001; Soria et al., 2000), other publications described pitfalls in such works, questioned the interpretations and demonstrated that reproducible protocols were not yet available to produce beta cells from ES cells (Hansson et al., 2004; Rajagopal et al., 2003).

Thus, at that point, functional beta cells have not yet been generated in large quantities from ES cells with the exception of one recent publication where beta cells developed from hES cells (D'Amour et al., 2006). However, such cells did not secrete insulin upon glucose stimulation.

A second approach was to derivate beta cell lines from beta cell tumours derived from transgenic mice expressing SV40 T antigen under the control of the insulin promoter (Efrat et al., 1995; Efrat et al., 1993; Efrat et al., 1988; Hanahan, 1985; Knaack et al., 1994; Miyazaki et al., 1990). These cell lines have been extremely useful for detailed study of rodent beta cells. However, as many differences exist between rodent and human beta cells, these beta cells cannot be used for human diagnosis or therapy. Also, since these beta cell lines were obtained by gene transfer in fertilized eggs, such a method is restricted to animal models without any possible transfer to human.

A third approach has been carried out by Ravassard et al. (2011). These authors described the obtention of a stable functional human beta cell line, designated EndoC-βH1, with glucose-inducible insulin secretion by using human foetal pancreases cells transduced with lentiviral vectors expressing SV40LT under the control of the insulin promoter. In this approach, the transduced pancreases cells were grafted into SCID mice so that they could develop into pancreatic tissue. The human beta cells differentiated, expressed SV40LT concomitantly with insulin, proliferated, and formed insulinomas. These insulinomas were next transduced with a lentiviral vector that expressed hTERT, and the hTERT-transduced insulinomas cells were then regrafted into other SCID mice in order to further amplify the proliferating beta cells. After removing the transplanted tissue from these SCID mice, cells were dissociated and then expanded in culture as cell lines. The resulting EndoC-βH1 cells contained 0.48 µg of insulin per million cells, were stable at least for 80 passages, and expressed many specific beta cell markers, without any substantial expression of markers of other pancreatic cell types. EndoC-βH1 cells secrete insulin in response to glucose stimulation, and insulin secretion is enhanced by known secretagogues, such as exendin-4, glibenclamide, and leucine. Finally, transplantation of EndoC-βH1 cells into mice with chemically-induced DM normalizes their glycaemia.

However it is of interest to obtain beta cells generated from a more mature post natal pancreas. In particular, embryonic pancreases can only be obtained after termination of pregnancy, which may raise ethical or legal questions in a number of countries. Thus it would be preferable to use non-embryonic material for generating human pancreatic beta cell lines.

Several attempts have been made to generate human beta cell lines from many human pancreatic sources, such as adult islets or insulinomas. However, insulin production by these cells was extremely low or these cells were capable of producing insulin only over a few passages (de la Tour et al., 2001; Demeterco et al., 2002; Gueli et al., 1987; Ju et al., 1998; Levine et al., 1995; Soldevila et al., 1991). In 2005, Narushima et al (Narushima et al., 2005) reported that they successfully established a functional human beta cell line (NAKT-15) from freshly isolated adult pancreatic islet cells transduced with a Moloney retrovirus expressing the SV40 Large T antigen. However, serious doubts have been raised regarding this work. In particular, gene transfer by such retroviral vectors occurs only in cells actively replicating at the time of infection (Miller D G et al, 1990), while adult pancreatic cells are very poorly mitotic (see Chen et al, 2011 and Kohler et al, 2010). It is thus likely that the NAKT-15 cell line is not a functional human beta cell line, as claimed, and that the method described in Narushima et al. does not enable the skilled person to obtain such a functional human beta cell line. Indeed, the work of Narushima et al. has not been reproduced, either by the authors or by other laboratories, since the original publication.

Meier J J. et al, (2008) showed that human post-natal beta-cells mass increase is due to the active replication of differentiated beta-cells and not to remaining progenitor cells. Yet these proliferating differentiated cells are incompetent to produce functional beta cell lines. Ravassard et al. (2011) attempted to generate a functional human beta cell line from adult human islets transduced by lentiviral vectors. The transduced cells survived after their transplantation into immuno-incompetent mice, but did not then develop into insulinomas. These observations were consistent with those obtained in another communication reporting that adult beta cells are refractory to transformation using multiple oncogenic mutants (Gidekel Friedlander et al, 2009).

As of today, the formation of insulinoma from human non-foetal cells has never been observed, and it has been considered impossible to obtain human beta cell lines from non-foetal pancreatic material (Ravassard et al., 2011).

Thus, there is still a need for a reliable and reproducible method for developing a functional human beta cell line from non-foetal pancreatic material.

DESCRIPTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The practice of the present invention employs, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook et al, 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et ah, eds., 1987, and periodic updates); PCR: The Polymerase Chain Reaction, (Mullis et al, ed., 1994); A Practical Guide to Molecular Cloning (Perbal Bernard V., 1988); Phage Display: A Laboratory Manual (Barbas et al., 2001). Enzymatic reactions and purification techniques are performed according to manufacturer's specifications, as commonly accomplished in the art or as described herein.

It is thus an object of the invention to provide an alternative method for producing human pancreatic beta cell lines. In particular, the invention is directed to a method for producing human beta cell lines from a non-foetal human pancreas. As used herein, a "beta cell" is a cell of the islets of Langerhans of the pancreas which secretes the hormone insulin in response to glucose and other secretagogues. A "human pancreatic beta cell" or "human beta cell" (these terms are synonymous in the context of the present application and should thus be construed to convey the same meaning) is a beta cell of human origin.

The present inventors have now devised a new strategy for generating human beta cell lines from non-foetal tissue materials. They have surprisingly discovered that, by using a sub-grafting method with neonatal pancreatic tissues, the pancreatic cells were capable of forming insulinoma-structures, under specific conditions. These insulinoma-structures contain human functional beta cells, whose sub-grafting results in a specific enrichment in beta cells, ultimately leading to the production of homogenous human beta cell lines which can be further amplified to clinical and commercial scale. By repeating the enrichment and amplification steps, the inventors were capable of obtaining repeatedly cell lines which can be amplified for testing, diagnosis or therapeutic use.

Accordingly, the present invention relates to a method for specifically establishing and amplifying human beta cells from non-foetal pancreatic tissues.

Several independent human beta cell lines are thus generated. Such lines express insulin and have a gene expression profile that resembles to adult beta cells. In addition, when transplanted under the kidney capsule of diabetic mice they are capable of normalizing blood glucose. Furthermore, the human beta cell lines are capable of normalizing glycemia of diabetic mice. By performing intraperitoneal glucose load, these animals utilize normally the glucose load, demonstrating their insulin secretion capabilities. Moreover, their cell line is able to respond to glucose stimulation and is therefore fully functional.

This opens perspective towards clinical use of beta cells in the treatment of diabetes. The new process for obtaining insulin-secreting cells by the method of the invention provides an abundant source of beta-cells.

The human beta cell lines obtained with the method of the invention can be efficiently used to detect the presence of auto-antibodies found in sera of diabetic patients and thereby have a great potential for diagnosis of type I diabetes. These beta cells are also being used to generate and amplify ad infinitum human beta cell lines which form master cell batches for cellular therapy.

In a first embodiment, the invention is directed to a method of preparing human pancreatic beta cells or human beta cell tumors, said method comprising the steps of:

a) dissociating neonatal human pancreatic tissue with collagenase in order to obtain neonatal human pancreas cells, b) transducing and co-transducing the neonatal human pancreas cells obtained in step a) with i) a lentiviral vector expressing SV40 LargeT antigen under the control of the insulin promoter or ii) with a lentiviral vector expressing SV40 LargeT antigen under the control of the insulin promoter and a lentiviral vector expressing hTERT under the control of the insulin promoter, or iii) a lentiviral vector expressing both SV40 LargeT antigen and hTERT, c) introducing the transduced neonatal pancreas obtained in b) into the kidney capsule of a severe compromised immunodeficiency (scid) non-human animal;

d) allowing the transduced pancreas cells to develop insulinoma-like structures, wherein neonatal human pancreases cells in insulinoma-like structures have differentiated in insulin-producing pancreatic beta cells;

e) micro-dissecting the insulinoma-like structures obtained in step d), dissociating the cells thereof, and optionally transducing the said cells with a lentiviral vector expressing an antibiotic resistance gene under the control of the insulin promoter, f) sub-transplanting of the cells obtained in step e) into the kidney capsule of a new scid non-human animal;

g) allowing the sub-transplanted cells in step f) to develop and regenerate insulinoma-like structures, wherein said newly developed insulinoma-like structures are enriched in insulin producing pancreatic beta cells;

h) micro-dissecting of insulinoma-like structures obtained in step g), dissociating and collecting the cells thereof, i) optionally, sub-transplanting the cells obtained in step g) into the kidney capsule of a new scid non-human animal, hence allowing further enrichment and amplification of insulin producing pancreatic beta cells;

j) optionally repeating step f), g) and h) until the appropriate amount of insulin producing pancreatic beta cells is obtained.

The term "pancreatic tissue" as used herein refers to a tissue obtained or derived from the pancreas; likewise, the term "pancreatic cells" refers herein to cells obtained or derived from pancreas. As used herein, the term "immature pancreatic cells" refers to cells which may be obtained from foetal pancreas or stem cells that have gone through a first differentiation in endodermic cells.

A "neonatal human pancreatic tissue" according to the invention is a tissue of a pancreas obtained from an individual who has been through birth. Thus encompassed by the present invention are tissues obtained from individuals at all ages of life. On the other hand, the present invention does not relate to the use of embryonic material to obtain beta cell lines. Preferably, the said individuals are less than 5-year old; more preferably, the said individual are less than 1-year old; even more preferably, the said individuals are less than 6-month old; still more preferable, the said individuals are less than 3-month old; most preferably, the said individuals are less than 1-month old.

The pancreatic tissue according to the invention can be recovered by surgery from one individual. The pancreatic tissue according to the invention can consist of the whole pancreas of the said individual or only a portion of the said pancreas. In one embodiment, the pancreatic tissue has been frozen after being harvested. In another embodiment, the pancreatic tissue used in the method of the invention is fresh. Thus, according to that specific embodiment, the method of the invention comprises a step of harvesting the pancreatic tissue prior to step a).

By "collagenase", it is herein referred to an enzyme belonging to the matrix metalloproteinase (MMP) family which is capable of breaking the peptide bonds in collagen. A collagenase according to the invention can be either of bacterial or animal origin. Bacterial collagenases differ from vertebrate collagenases in that they exhibit broader substrate specificity. Unlike animal collagenases, bacterial collagenase can attack almost all collagen types, and is able to make multiple cleavages within triple helical regions. Preferably, the collagenase of the invention is a bacterial enzyme; more preferably, it is an enzyme secreted by the anaerobic bacteria *Clostridium histolyticum*. In a preferred embodiment, the collagenase used in the invention is selected from the group consisting of collagenases Type I-S, Type IA, Type IA-S, Type II, Type II-S, Type IV, Type IV-S, Type V, Type V-S, Type VIII, Type XI and Type XI-S. In the most preferred embodiment, the collagenase of the invention is collagenase XI.

The concentration of the collagenase used in step a) of the method of the invention is preferably inferior or equal to 5 mg/mL; more preferably, to 4 mg/mL; even more preferably, to 3 mg/mL; still more preferably, to 2 mg/mL; yet even more preferably, to 1 mg/mL. In the most preferred embodiment, said collagenase is used at 1 mg/mL. According to the invention, neonatal human pancreatic tissue is dissociated with collagenase for at least 10 minutes; preferably for at least 15 minutes; more preferably at least 20 minutes; even more preferably at least 25 minutes; still more preferably at least 30 minutes; most preferably for 30 minutes at about 37° C. For dissociation to occur, the above-mentioned pancreatic tissues are preferably suspended in an appropriate medium comprising PBS+20% FCS.

Transduction of the neonatal human pancreases cells obtained from the dissociation of the pancreatic tissues with lentiviral vectors is carried out according to the methods known to the person of skills in the art (see e.g. Ravassard et al., 2011, and references therein). Lentiviral vectors are vectors derived from a lentivirus such as HIV 1. They are able to transduce non-dividing as well as dividing cells and sustain expression of heterologous nucleic acid sequences in several target tissues in vivo, including brain, liver, muscle, and hematopoietic stem cells. A great number of lentiviral vectors are already known to the person of skills in the art; any one of these vectors can be used in the context of the present invention, provided that they express at least the SV40 Large T antigen and/or hTERT, under the control of the insulin promoter. The person of skills in the art is directed to Ravassard et al (2011) and WO 20088/102000 where examples of such lentiviral vectors have been described It may be advantageous to de-immortalize the human beta cells of the invention in certain conditions. For example, if administration of the said cells to a patient is contemplated, it is safer to remove the oncogenes carried by the vectors. Lentiviral vectors can thus be constructed to allow reversible or conditional immortalization, so that at least one Lox P site may be introduced. More preferably, the vectors according to the invention are constructed so that the SV40 LargeT and/or the hTERT transgenes are located within two Lox P site. Said transgenes are removed by expressing the Cre recombinase in the beta cells. For example the cells obtainable by the above method are transduced by a vector or plasmid expressing a Cre recombinase and reversion occurs. Of course, the skilled in the art may choose to use the FRT/FLP system to remove said transgenes. Methods for reverting immortalized cells are described in WO 01/38548.

In a particular embodiment, the lentiviral vector expressing SV40 LargeT and the lentiviral vector expressing hTERT further comprise a LoxP or a FRT site, provided that site specific recombination sites are different in both vectors.

Negative selection step can also be performed after the action of the Cre or FLP recombinase. This further step allows selecting only the cells in which the immortalization genes SV40 LargeT and hTERT, as well as the antibiotic resistance gene, have been removed. These cells can be frozen, stored and optionally encapsulated, until they are transplanted into diabetic patients.

The negative selection marker gene can be, for example, the HSV-TK gene and the selective agent acyclovir-gancyclovir. Or the negative selection markers are the hypoxanthine phosphoribosyl transferase (HPRT) gene and the guanine-phosphoribosyl-transferase (Gpt) gene and the selective agent is the 6-thioguanine. Or the negative selection marker is the cytosine deaminase gene and the selective agent is the 5-fluoro-cytosine. Thus in a preferred embodiment, the said negative marker gene is selected from the group constituted by the HSV-TK gene, the hypoxanthine phosphoribosyl transferase (HPRT) gene, the guanine-phosphoribosyl-transferase (Gpt) gene, and the cytosine deaminase gene. Other examples of negative selection marker proteins are the viral and bacterial toxins such as the diphteric toxin A (DTA). These negative selection genes and agents and their use are well known to the person of skills in the art and need not be further detailed here.

The transduced cells are then introduced into at least one kidney capsule of severe compromised immunodeficiency (scid) animals. A scid animal is an animal lacking T and B lymphocytes and failing to generate either humoral or cell mediated immunity. The scid non-human animal as referred herein can be selected among bovines, porcines, horses, sheep, goats, primates excepted humans, rodents such as mice, rats, hamsters. The said scid non-human animal can carry at least one other type of mutation leading to immunodeficiency. The said scid non-human animal can be a non-obese diabetic/severe combined immunodeficiency (NOD/scid) animal. A NOD/scid animal is an animal lacking T and B lymphocytes, which thus fails to generate either humoral or cell-mediated immunity.

In a preferred embodiment, the NOD/scid animal used in the method of the invention is a mouse. NOD/scid mice are known in the literature and are commercially available from suppliers such as Charles River or Jackson Laboratory. Preferably the NOD/scid mouse used in the method of the invention is of any age of development, preferably sufficiently old so that a graft into the kidney capsule can be performed. Preferably, the NOD/scid mice are about of the 2 to 15 weeks of development, more preferably to 6 to 8 weeks of development.

Optionally, the cells are further transduced at step c) with another lentiviral vector expressing an antibiotic resistance gene under the control of the insulin promoter. The antibiotic resistance gene is selected in the group consisting of hygromycin resistance gene, neomycin resistance genes, tetracyclin resistance gene, ampicillin resistance gene, kanamycin resistance gene, phleomycin resistance gene, bleomycin resistance gene, geneticin resistance gene, carbenicillin resistance gene, chloramphenicol resistance gene, puromycin resistance gene, blasticidin-S-deaminase gene. In a preferred embodiment, said antibiotic resistance gene is a neomycin resistance gene. In this case, the selective agent is G418.

The above-defined method includes collecting the human functional pancreatic beta cells obtained at step g) which form a homogenous cell population. The cell population can further be cultured in vitro to establish a human functional beta cell line. At this stage, the cells derived from the successive sub-grafts contained the SV40 LargeT and/or the hTERT and the antibiotic resistance transgenes. Thus, the cell lines obtainable by the above method are immortalized and depending on the end point they may or may not be reversed (de-immortalized). In particular, de-immortalization can be useful when a therapeutic use of the cells of the invention is contemplated.

The above method to prepare human functional pancreatic Beta cells is particularly useful for testing and screening candidate medicament for treating diabetes in vivo after graft in non-human animals, such as mice or rats, or in vitro.

In this regard, and in one specific embodiment, the above method can be practiced to prepare large amount of human functional pancreatic Beta cells for testing and screening purposes as well as for in vitro diagnosis allowing classification of patients in type 1 or 2 diabetes. Here, the cells may be de-immortalized. On the contrary, with the above method, steps f), g) and h) can be repeated as many times as necessary to obtain large amount of insulinoma or isolated human beta cells thereof and these cells may further be amplified in culture in vitro ad infinitum. Cross section of Beta cell tumors, cells derived thereof or protein extract from these cells can be bound or adsorbed to a solid support (for example polylysine coated plates) and reacted with the plasma serum of individuals. After incubation, the serum is washed out and the presence or absence of autoantibodies against different surface antigens specific to autoimmunity associated with diabetes is revealed (for example by means of labeled anti-human Ig).

Therefore, in a second aspect, the invention is aimed at human beta cell tumors or insulinomas, or human pancreatic beta cells obtainable by the above-described method. These human beta cell tumors or human pancreatic beta cells display at least one of the following features:
Carboxypeptidase-A negative
transcriptional factor Pdx1 positive
transcription factor MafA positive
proconvertase Pcsk1 positive
expression of Glucose transporter Glut2
expression of Kcnj11 and Abcc8 coding for subunits of the potassium channel
expression of zinc transporter Znt8 (Slc30a8), or
expression of insulin.

Human beta cell tumors or human pancreatic beta cells as defined above are also positive to reaction with anti-insulin, anti-GAD and/or anti-IA2 antibodies and can be maintained and grown in culture in a medium free of serum and on Matrigel and fibronectin coated wells. Thus, the invention also contemplates a cell culture comprising the above-described human pancreatic beta cells in culture in a medium free of serum comprising Matrigel and fibronectin. This cell culture allows to expand and to establish immortalized human pancreatic beta cell lines.

Moreover, the cell lines obtainable by the above-described method may be de-immortalized, so that they can be used for example for testing and screening purposes as well as for in vitro diagnosis allowing classification of patients in type 1 or 2 diabetes.

The above described method to prepare human functional pancreatic beta cells is particularly useful for testing and screening candidate medicaments for treating diabetes in vivo after graft in non-human animals, such as mice or rats, or in vitro. Specifically, the invention relates to a method for testing and screening candidate medicaments for treating diabetes, said method comprising the step of administering a candidate medicament to a non-human animal grafted with the human pancreatic cells of the invention. In a more specific embodiment, the method comprises prior steps of obtaining the said beta cells according to the methods described above, and grafting the said cells into the said non-human animal. The said non-human animal is preferably a scid non-human animal, as described above.

The present invention also relates to a method of in vitro diagnosis of diabetes. Cross section of beta cell tumors, cells derived thereof or protein extract from these cells can be bound or adsorbed to a solid support (for example polylysine coated plates) and reacted with the plasma serum of individuals. After incubation, the serum is washed out and the presence or absence of autoantibodies against different surface antigens specific to autoimmunity associated with diabetes is revealed (for example by means of labeled anti-human Ig).

Thus, a first embodiment of the invention relates to a method of in vitro diagnosis of diabetes comprising linking or adsorbing human beta cell tumors or human pancreatic beta cells as described above, or protein extract from said cells, to a solid support and reacting with the plasma serum of individuals, detecting the presence or absence of autoantibodies against different surface antigen specific to type 1 or type 2 diabetes, such as Islet Cells Antibodies (ICA), selected for example from Insulin autoantibodies (IAA) and glutamic acid decarboxylase antibodies (GADA).

Preferably, sera from patient and control are added on the said tissue sections of the said human beta cell tumors or human beta cells, and incubated with a labeled anti-human IgG, such as a fluorescent labeled conjugated anti-human IgG, in order to reveal the presence or absence of auto-antibodies associated with diabetes in the sera of said patient. In this embodiment, the presence of auto-antibodies is indicative of diabetes.

The presence or absence of auto-antibodies associated with diabetes in the sera of the said patient can also be detected by a western blot of a protein extract of the said human beta cell tumors or the said human pancreatic beta cells. In this case, the presence or absence of auto-antibodies associated with diabetes in the sera of said patient is revealed with labeled anti human IgG, such as HRP conjugated anti human IgG. Alternatively, the presence or absence of auto-antibodies associated with diabetes in the sera of the said patient is detected by an ELISA test in which the wells plates are coated with a protein extract of the said human beta cell tumors or the said human pancreatic beta cells. According to this embodiment, the said protein extract is incubated with sera from patient and control, and the presence or absence of auto-antibodies associated with diabetes in the sera of said patient is revealed with labeled anti human IgG, such as HRP conjugated anti human IgG.

In another aspect, a method of in vitro diagnosis of diabetes comprises reacting section of beta cell tumors, cells derived thereof or protein extract of these cells obtainable by the method depicted above with the plasma serum of individuals, detecting the presence or absence of autoantibodies against different surface antigen specific to type 1 or type 2 diabetes, such as Islet Cells Antibodies (ICA), or more specific antibodies recently identified like antibodies against Insulin autoantibodies (IAA) and glutamic acid decarboxylase antibodies (GADA) or IA-2 antibodies (IA2A) or specific unknown antibodies. The identification of known or new antibodies can be performed by immunoblot or dot-blot for example.

This aspect of the invention provides for the first time a kit that can be prepared at a commercial scale for diabetes classification. More particularly, specific autoantibodies are Islet Cells Antibodies (ICA) selected from Insulin autoantibodies (IAA) and glutamic acid decarboxylase antibodies (GADA). Indeed, these antigens are expressed at the surface of the beta cell tumors or cells derived thereof obtainable according to the above method. Thus, embraced herein is a diagnostic kit for diabetes, said kit comprising beta cell tumors or human functional pancreatic beta cells obtainable by the above method, or proteins extract there from, optionally bond or adsorbed to a solid support.

In another embodiment, the cells as described above are cultured in vitro and human pancreatic beta cell lines are established for screening compounds capable of modulating insulin secretion. The present invention thus also provides a method for screening compounds capable of modulating insulin secretion, said method comprising the steps of: a) contacting the human pancreatic beta cells of the invention with a test compound, and b) detecting insulin secretion and measuring the level of insulin secretion. Insulin secretion can be detected by any of the means known to the person of skills in the art, as detailed in e.g. the experimental examples below, in Ravassard et al, and in WO 2008/102000. According to a preferred embodiment, the method of the invention comprises a step of comparing the level of secreted insulin obtained in step b) with at least one control level. The said control level corresponds to the level of insulin produced by a cell line which is known to secrete insulin, such as the EndoC-βH1 cell line of Ravassard. Alternatively, the said control level corresponds to the level of insulin produced by a cell line which is known to not produce any insulin. In a further preferred embodiment, the secreted insulin level of step b) is compared with two control levels, one corresponding to the level of insulin produced by a cell line which is known to secrete insulin and the other one corresponds to the level of insulin produced by a cell line which is known to not secrete insulin. In yet another preferred embodiment, the method of invention comprises a prior step of obtaining the human pancreatic beta cell line according to the method described above.

In still another embodiment, the above method is directed to the establishment of master cell banks for cell therapy of diabetes. Here, the method further includes de-immortalizing the cells. Said de-immortalization of the cells includes a step of removing the SV40 Large T and the hTERT transgene from the lentiviral vectors. Preferably the transgene are excised by site-specific recombination with a site-specific recombinase such as Cre or Flp, as described above.

In still another embodiment, the invention relates to the beta cell tumors and isolated cells thereof obtainable by the above method. As explained, both immortalized and de-immortalized are encompassed herein.

The invention also concerns the use of said cells for testing or screening candidate medicaments for the treatment of diabetes, for in vitro diagnosis as explained above and for cell therapy of diabetes.

The present invention also provides a method of regenerating pancreas function in an individual afflicted with diabetes, the method comprising a step of administrating an effective amount of the human functional pancreatic cells as defined above, said cells being reverted to a primary beta cell phenotype, into said individual. In a preferred embodiment, the said cells are transplanted within the said individual. In another preferred embodiment, the said method of regenerating pancreas function comprises a prior step of obtaining the said human pancreatic beta cells by the method described above.

The invention also relates to a pharmaceutical composition comprising a pharmaceutical acceptable carrier and an effective amount of the human functional pancreatic cells as defined above, said cells being optionally encapsulated.

An "effective amount" is an amount sufficient to effect beneficial or desired clinical results. An effective amount, for example from $10^5$ to $10^9$ cells, can be administered in one or more applications, although it is preferable that one administration will suffice. For purposes of this invention, an effective amount of stem cells precursors of pancreatic beta cells is an amount that is sufficient to produce differentiated pancreatic cells which are able to restore one or more of the functions of the pancreas. It is contemplated that a restoration can occur quickly by the introduction of relatively large numbers of pancreas cells, for example greater than $10^9$ cells. In addition, it is also contemplated that when fewer pancreatic cells are introduced, function will be restored when the pancreas cell or cells are allowed to proliferate in vivo. Thus, an "effective amount" of pancreatic cells can be obtained by allowing as few as one pancreas cell sufficient time to regenerate all or part of a pancreas. Preferably, an effective amount administered to the individual is greater than about $10^1$ pancreas cells, preferably between about $10^2$ and about $10^{15}$ pancreas cells and even more preferably, between about $10^3$ and about $10^{12}$ pancreas cells. In terms of treatment, an "effective amount" of pancreatic cells is the amount which is able to ameliorate, palliate, stabilize, reverse, slow or delay the progression of pancreas disease, such as diabetics.

As used herein, "pharmaceutically acceptable carrier" includes any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art. A typical pharmaceutical composition for intravenous infusion could be made up to contain 250 ml of sterile Ringer's solution, and 100 mg of the combination. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the $18^{th}$ and $19^{th}$ editions thereof, which are incorporated herein by reference.

Methods of introducing cells into individuals are well known to those of skills in the art and include, but are not limited to, injection, intravenous or parenteral administration. Single, multiple, continuous or intermittent administration can be effected. The human beta cells of the invention can thus be introduced into any of several different sites, including but not limited to the pancreas, the abdominal cavity, the kidney, the liver, the celiac artery, the portal vein or the spleen. Preferably, the said beta cells are deposited in the pancreas of the individual.

The human pancreatic beta cells of the invention can be useful for regenerating pancreatic functions. The said cells can also be administered to an individual suffering from a pancreatic disorder in order to treat said disorder. Thus the present invention also contemplates a method for treating a pancreatic disorder with human pancreatic beta cells obtained by the method of the invention, comprising the administration of the said human pancreatic beta cells to a patient in need thereof. According to a preferred embodiment, the method of the invention comprises a prior step of obtaining the said human pancreatic beta cells from a human pancreatic tissue. In a further preferred embodiment, the human pancreatic tissue is obtained from the said patient in need of a treatment.

It is thus another aspect of the present invention to provide pancreatic cells of the invention as a medicament. More precisely, the present invention relates to the use of human pancreatic beta cells of the invention for preparing a medicament to treat a human pancreatic disorder. Yet another aspect of the invention relates to the human pancreatic beta cells of the invention for use in treating a human pancreatic disorder.

A human pancreatic disorder according to the invention is diabetes, hypoglycemia, or any pathology associated with a dysfunction of the digestive enzymes. Preferably, a human pancreatic disorder is insulin-dependent diabetes (T1D),

FIGURE LEGENDS

FIG. 1 discloses the staining of a human neonatal pancreatic tissue which was transduced with lentiviruses expressing SV40T under the control of the rat insulin promoter, transplanted to SCID mice and explanted 12 days later. A large number of insulin-positive cells stain positive for SV40T.

Figure 2:
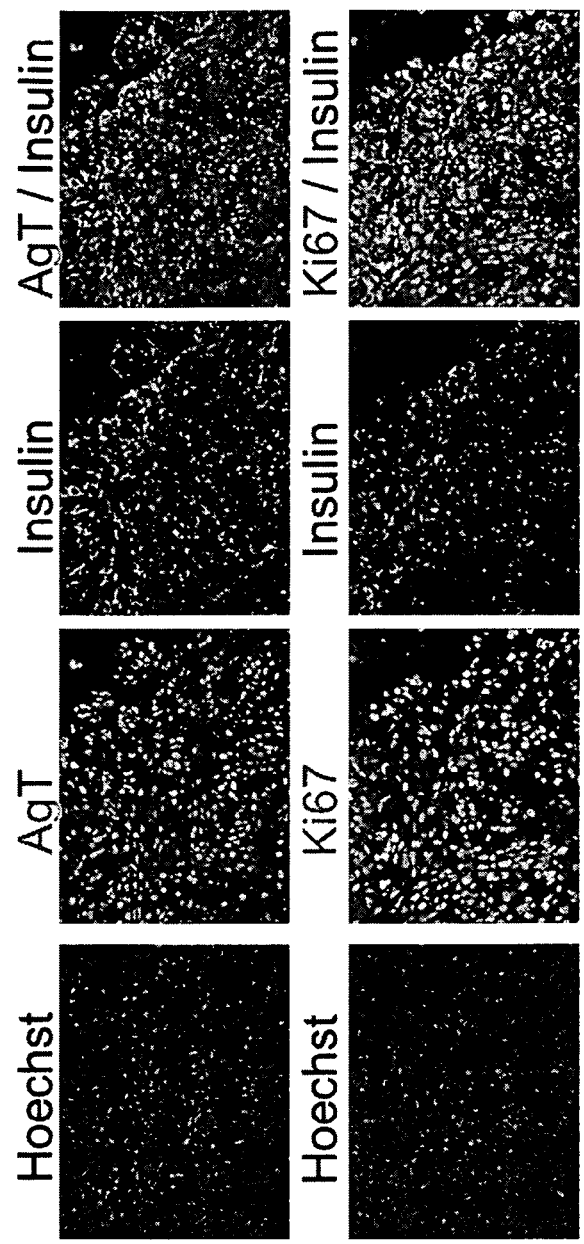

FIG. 2 discloses the staining using anti-insulin, anti-SV40T and anti-Ki67 antibodies of human neonatal pancreatic tissue which was transduced with lentiviruses expressing SV40T under the control of the rat insulin promoter, transplanted to SCID mice and explanted seven months later. Beta cell mass (insulin-positive cells) expanded with major proliferation of insulin-positive cells.

FIG. 3 shows the staining using anti-insulin, anti-SV40T and anti-PDX1 antibodies of human insulinoma derived from sub-grafted SCID mice.

The examples that follow are merely exemplary of the scope of this invention and content of this disclosure. One skilled in the art can devise and construct numerous modifications to the examples listed below without departing from the scope of this invention.

EXAMPLES

DNA Constructs and Lentiviral Vector Productions

The lentiviral vectors, pTRIP ΔU3.RIP405-SV40LT loxP and pTRIP ΔU3.RIP405-hTERT loxP, have been constructed by adding a loxP site in the 3'LTR region of the pTrip ΔU3.RIP405-SV40LT/hTERT previously described (Ravassard et al, 2009). Both pTRIP ΔU3 vectors were digested by KpnI and PadI to remove the 3'LTR region. The 3'LTRloxP region of the SIN-RP-LTcDNA-WHV-U3loxP (provided by Bernard Thorens) was amplify by PCR and next digested by KpnI and PadI and then ligated into the two linearized pTrip vectors. The Lentiviral vector stocks were produced by transient transfection of 293T cells by encapsidation of the p8.9 plasmid (ΔVprΔVifΔVpuΔNef) (Zufferey et al, 1997), pHCMV-G that encoded the VSV glycoprotein-G) (Zufferey et al, 1997) and the pTRIP ΔU3 recombinant vector, as previously described (Zufferey et al., 1997). The supernatants were treated with DNAse I (Roche Diagnostic) prior to their ultracentrifugation, and the resultant pellets were re-suspended in PBS, aliquotted, and then frozen at −80° C. until use. The amount of p24 capsid protein was quantified by the HIV-1 p24 antigen ELISA (Beckman Coulter). All transductions were normalized relative to p24 capsid protein quantification.

Human Tissues

Human neonatal pancreatic pieces from the tail of pancreas were obtained following surgery of children less than one year old in compliance with the French bio-ethic legislation.

Gene Transfer

The pancreatic tissue was cut in 1 mm square pieces in foetal calf serum, treated with collagenase XI (1 mg/ml RPMI) (Sigma-Aldrich) during 30 minutes at 37° C. and next rinsed twice in PBS containing 20% foetal calf serum. Newborn pancreases were transduced with pTRIP ΔU3.RIP405-SV40LT loxP as previously described (Castaing 2005, Scharfmann 2008). Briefly, tissues were transduced with a total amount of lentiviral vectors corresponding to 2 μg of p24 capside protein for two hours at 37° C. in 200 μl of DMEM that contained 5.6 mM glucose, 2% bovine serum albumin fraction V (BSA, Roche diagnostics), 50 μM 2-mercaptoethanol, 10 mM nicotinamide (Calbiochem), 5.5 μg/ml transferrin (Sigma-Aldrich), 6.7 ng/ml selenite (Sigma-Aldrich), 100 U/ml penicillin, and 100 m/ml streptomycin and 10 μg/ml DEAE-dextran. Tissues were then washed twice with medium culture and kept on culture overnight until transplantation into scid mice.

Animals and Transplantation into SCID Mice

Male SCID mice (Harlan) were maintained in isolators. Using a dissecting microscope, pancreases or islets were implanted under the kidney capsule, as previously described (17, 33). At different time points after transplantation, the mice were sacrificed, the kidney removed, and the graft dissected. All animal studies and protocols were approved by the Veterinary Inspection Office in compliance with the French legislation under agreement number B75-13-03.

Immunostaining of Pancreatic Explants and Cell Lines

Tissues were fixed in 3.7% formaldehyde prior to their embedding in paraffin. For immunohistochemistry, sections (4-μm thick) were prepared and processed, as described previously (Attali et al, 2007). The following antibodies were used for immunostaining: guinea pig anti-insulin antibody (1/500, DakoCytomation); rabbit anti-glucagon (1/1000, Euromedex); rabbit anti-somatostatin antibody (1/500, DakoCytomation); rabbit anti-human PDX1 antibody (1/2000) (45); rabbit anti-SOX9 antibody (1/500, Millipore); rabbit anti-carboxypeptidase A antibody (1/600, AbD Serotec); mouse anti-SV40LT (1/50, Calbiochem Merck Biosciences) and mouse anti-human Ki67 antigen (1/50, DakoCytomation). The secondary antibodies were fluorescein anti-rabbit antibody (1/200; Jackson Immunoresearch Laboratories, Beckman Coulter); Texas-red anti-guinea pig antibody (1/200; Jackson Immunoresearch Laboratories).

Digital images were captured using a cooled three-chip charge coupled-device camera (Hamamatsu C5810; Hamamatsu) that was attached to a fluorescent microscope (Leica; Leitz).

Results

Small pieces of neonatal pancreatic rudiments were transduced with a lentiviral vector that expressed SV40LT under the control of a 405-nucleotide-long fragment of the rat insulin II promoter. The resultant transduced tissues were next transplanted under the kidney capsule of SCID mice. The pancreatic tissue was explanted at day 12 and seven months. At day 12, immunohistochemical analysis using anti-insulin and anti-SV40T antibodies indicated that nearly 50% of insulin-positive cells stained positive for SV40T, demonstrating efficient transduction and survival (FIG. 1). After 7 months, immunohistochemical analysis using anti-insulin, anti-SV40T and anti-Ki67 antibodies demonstrated major beta cell proliferation (FIG. 2). As expected, proliferating beta cells stained positive for the transcription factor PDX1 and negative for glucagon and somatostatin (data not shown). At this stage, some of the cells were sub-transplanted to new SCID mice as described (Ravassard et al, 2011). One month later, glycemia decreased in such transplanted mice, a sign of rapid insulinoma formation.

A cell line was derived from such an insulinoma. These cells were stained for immunocytochemistry. As shown in FIG. 3 the staining is very rich for insulin and PDX1 and the large T antigen is present.

REFERENCES

Asfari, M., Janjic, D., Meda, P., Li, G., Halban, P., and Wolheim, K. (1992). Establishment of 2-mercaptoethanol-dependent differentiated insulin secreting cell lines. *Endocrinology* 130, 167-178.

Attali M, Stetsyuk V, Basmaciogullari A, Aiello V, Zanta-Boussif M A, Duvillie B, Scharfman R (2007) Control of beta-cell differentiation by the pancreatic mesenchyme. *Diabetes* 56(5): 1248-1258.

Castaing, M., Duvillie, B., Quemeneur, E., Basmaciogullari, A., and Scharfmann, R. (2005a). Ex vivo analysis of acinar and endocrine cell development in the human embryonic pancreas. *Dev Dyn* 234, 339-345.

Chen H., Gu X., Su I., Bottino R., Contreras J. L., Tarakhovsky A. and Kim S. K. (2011) Polycomb protein Ezh2 regulates pancreatc beta-cell ink4a/arf expression and regeneration in diabetes mellitus, *Genes & development:* 23:975-985

D'Amour, K. A., Bang, A. G., Eliazer, S., Kelly, O. G., Agulnick, A. D., Smart, N. G., Moorman, M. A., Kroon, E., Carpenter, M. K., and Baetge, E. E. (2006). Production of pancreatic hormone-expressing endocrine cells from human embryonic stem cells. *Nat Biotechnol* 24, 1392-1401.

de la Tour, D., Halvorsen, T., Demeterco, C., Tyrberg, B., Itkin-Ansari, P., Loy, M., Yoo, S. J., Hao, E., Bossie, S., and Levine, F. (2001). Beta-cell differentiation from a human pancreatic cell line in vitro and in vivo. *Mol Endocrinol* 15, 476-483.

Demeterco, C., Itkin-Ansari, P., Tyrberg, B., Ford, L. P., Jarvis, R. A., and Levine, F. (2002). c-Myc controls proliferation versus differentiation in human pancreatic endocrine cells. *J Clin Endocrinol Metab* 87, 3475-3485.

Efrat, S., Fusco-DeMane, D., Lemberg, H., al Emran, O., and Wang, X. (1995). Conditional transformation of a pancreatic Beta-cell line derived from transgenic mice expressing a tetracycline-regulated oncogene. *Proc Natl Acad Sci USA* 92, 3576-3580.

Efrat, S., Leiser, M., Surana, M., Tal, M., Fusco-Demane, D., and Fleischer, N. (1993). Murine insulinoma cell line with normal glucose-regulated insulin secretion. *Diabetes* 42, 901-907.

Efrat, S., Linde, S., Kofod, H., Spector, D., Delannoy, M., Grant, S., Hanahan, D., and Baekkeskov, S. (1988). β cell lines derived from transgenic mice expressing a hybrid insulin gene-oncogene. *Proc Natl Acad Sci USA* 85, 9037-9041.

Gazdar, A., Chick, W., Oie, H., Sims, H., King, D., Weir, G., and Lauris, V. (1980). Continuous, clonal, insulin- and somatostatin-secreting cell lines established from a transplantable rat islet cell tumor. *Proc Natl Acad Sci USA* 77, 3519-3523.

Gidekel Friedlander S Y, Chu G C, Snyder E L, Girnius N, Dibelius G, Crowley D, Vasile E, DePinho R A, Jacks T. (2009). Context-dependent transformation of adult pancreatic cells by oncogenic K-Ras. *Cancer Cell* 16(5):379-89.

Gueli, N., Toto, G., Palmieri, G., Carmenini, G., Delfino, A., and Ferrini, U. (1987). In vitro growth of a cell line originated from a human insulinoma. *Journal of Experimental and Clinical Cancer Research* 4, 281-285.

Hanahan, D. (1985). Heritable formation of pancreatic beta-cell tumours in transgenic mice expressing recombinant insulin/simian virus 40 oncogenes. *Nature* 315, 115-122.

Hansson, M., Tonning, A., Frandsen, U., Petri, A., Rajagopal, J., Englund, M. C., Heller, R. S., Hakansson, J., Fleckner, J., Skold, H. N., et al. (2004). Artifactual insulin release from differentiated embryonic stem cells. *Diabetes* 53, 2603-2609.

Ju, Q., Edelstein, D., Brendel, M. D., Brandhorst, D., Brandhorst, H., Bretzel, R. G., and Brownlee, M. (1998).

Transduction of non-dividing adult human pancreatic beta cells by an integrating lentiviral vector. *Diabetologia* 41, 736-739.

Knaack, D., Fiore, D. M., Surana, M., Leiser, M., Laurance, M., Fusco-DeMane, D., Hegre, O. D., Fleischer, N., and Efrat, S. (1994). Clonal insulinoma cell line that stably maintains correct glucose responsiveness. *Diabetes* 43, 1413-1417.

Köhler et al, Olewinski M., Tannapfel A., Schmidt W. E., Fritsch H., Meier J. J. (2010), Cell cycle control of beta-cell replication in the prenatal and postnatal human pancreas. *Am. J. Physiol. Endocrinol. Metab.* E221-E230

Levine, F., Wang, S., Beattie, G., Mally, M., Cirulli, V., Lopez, A., and Hayek, A. (1995). Development of a cell line from human foetal pancreas. *Transplantation proceedings* 27, 3410.

Meier J J., Buttler A. E., Saisho Y., Monchamp T., Galasso R., Bhushan A., Rizza R. A. Butler P. C. (2008), β-cell replication is the primary mechanism subserving the Postnatal Expansion of β-cell mass in humans, *Diabetes,* 57: 1584-1594

Miller D G, Adam M. A. and Miller A. D. (1990) Gene transfer by retrovirus vectors occurs only in cells that are actively replicating at the time of infection. *Mol Cell Biol.* 10:4239-4242

Miyazaki, J., Araki, K., Yamato, E., Ikegami, H., Asano, T., Shibasaki, Y., Oka, Y., and Yamamura, K. (1990). Establishment of a pancreatic beta cell line that retains glucose-inducible insulin secretion: special reference to expression of glucose transporter isoforms. *Endocrinology* 127, 126-132.

Narushima, M., Kobayashi, N., Okitsu, T., Tanaka, Y., Li, S. A., Chen, Y., Miki, A., Tanaka, K., Nakaji, S., Takei, K., et al. (2005). A human beta-cell line for transplantation therapy to control type 1 diabetes. *Nat Biotechnol* 23, 1274-1282.

Rajagopal, J., Anderson, W. J., Kume, S., Martinez, O. I., and Melton, D. A. (2003). Insulin staining of ES cell progeny from insulin uptake. *Science* 299, 363.

Ravassard P, Emilie Bricout-Neveu, Hazhouz Y, Pechberty S, Mallet J, Czernichow P, Scharfmann R. (2009) A new strategy to generate functional insulin-producing cell lines by somatic gene transfer into pancreatic progenitors. *PLoS One.* 4(3): e4731

Ravassard P, Hazhouz Y, Pechberty S, Bricout-Neveu E, Armanet M, Czernichow P, Scharfmann R. (2011), A genetically engineered human pancreatic β cell line exhibiting glucose-inducible insulin secretion. *J Clin Invest*. September 1; 121(9):3589-97

Santerre, R., Cook, R., Criscl, R., Sharp, J., Schidt, R., Williams, D., and Wilson, C. (1981). Insulin synthesis in a clonal cell line of simian virus 40-transformed hamster pancreatic beta cells. *Proc Natl Acad Sci USA* 78, 4339-4342.

Soldevila, G., Buscema, M., Marini, V., Sutton, R., James, R. F., Bloom, S. R., Robertson, R. P., Mirakian, R., Pujol-Borrell, R., and Bottazzo, G. F. (1991). Transfection with SV40 gene of human pancreatic endocrine cells. *J Autoimmun* 4, 381-396.

Soria, B., Roche, E., Berna, G., Leon-Quinto, T., Reig, J. A., and Martin, F. (2000). Insulin-secreting cells derived from embryonic stem cells normalize glycemia in streptozotocin-induced diabetic mice. *Diabetes* 49, 157-162.

Zufferey, R., Nagy, D., Mandel, R. J., Naldini, L., and Trono, D. (1997). Multiply attenuated lentiviral vector achieves efficient gene delivery in vivo. *Nat Biotechnol* 15, 871-875.

The invention claimed is:

1. A method of preparing human pancreatic beta cells or human beta cell tumors, wherein said human pancreatic beta cells or human beta cell tumors express insulin and PDX-1, said method comprising the steps of:
   a) dissociating neonatal human pancreatic tissue with collagenase in order to obtain neonatal human pancreas cells,
   b) transducing and co-transducing the neonatal human pancreas cells obtained in step a) with i) a lentiviral vector expressing only SV40 LargeT antigen under the control of the insulin promoter or ii) with a lentiviral vector expressing only SV40 LargeT antigen under the control of the insulin promoter and a lentiviral vector expressing only hTERT under the control of the insulin promoter, or iii) a lentiviral vector expressing both SV40 LargeT antigen and hTERT but no other oncogene,
   c) introducing the transduced neonatal pancreas obtained in b) into the kidney capsule of a first severe combined immunodeficiency (scid) mouse,
   d) allowing the transduced pancreas cells to develop insulinoma-like structures, wherein the neonatal human pancreas cells in insulinoma-like structures have differentiated in insulin-producing pancreatic beta cells;
   e) micro-dissecting the insulinoma-like structures obtained in step d), dissociating the cells thereof,
   f) sub-transplanting the cells obtained in step e) into the kidney capsule of a second scid mouse,
   g) allowing the sub-transplanted cells in step f) to develop and regenerate insulinoma-like structures, wherein said newly developed insulinoma-like structures are enriched in insulin producing pancreatic beta cells;
   h) micro-dissecting the insulinoma-like structures obtained in step g), and dissociating and collecting the cells thereof,
   i) optionally, sub-transplantating the cells obtained in step g) into the kidney capsule of a third scid mouse, to further enrich and amplify insulin-producing pancreatic beta cells; and
   j) optionally repeating steps f), g) and h) until an appropriate amount of insulin-producing pancreatic beta cells is obtained,
   wherein the insulin-producing pancreatic beta cells allow insulinoma formation and restoration of normoglycemia in diabetic SCID mice.

2. The method of claim 1, wherein the construction of the lentiviral vectors allows reversible or conditional immortalization.

3. The method of claim 1, wherein the lentiviral vectors comprise at least one Lox P site and the SV40 LargeT and/or hTERT genes are removed by the action of the Cre recombinase.

4. The method of claim 1, wherein the lentiviral vectors comprise at least one FRT site and the SV40 LargeT and/or hTERT genes are removed by the action of FLP recombinase.

5. The method of claim 1, wherein the lentiviral vector expressing SV40 LargeT and the lentiviral vector expressing hTERT further comprise a LoxP or a FLP site, provided that the site specific recombination sites are different in said vectors.

6. The method of claim 1, wherein a negative selection step is performed after the action of the Cre or FLP recombinase to select only the cells in which the immortalization genes SV40 LargeT and/or hTERT have been removed.

7. The method of claim 1, wherein said lentiviral vectors include at least one negative selection marker gene.

8. The method of claim 7, wherein the negative marker gene is selected from the group consisting of the HSV-TK gene, the hypoxanthine phosphoribosyl transferase (HPRT) gene, the guanine-phosphoribosyl-transferase (Gpt) gene, and the cytosine deaminase gene.

9. The method of claim 1, further comprising transducing the cells of step e) with a lentiviral vector expressing an antibiotic resistance gene under control of the insulin promoter.

10. The method of claim 9, wherein the antibiotic resistance gene is a neomycin resistance gene.

11. The method of claim 1, further comprising collecting the human pancreatic beta cells obtained at step j) to form an homogenous cell population and optionally culturing said population in vitro to establish a human functional beta cell line.

12. The method of claim 1, wherein said collagenase is collagenase XI.

13. The method of claim 1, further comprising one or more de-immortalizing step(s) including removing the SV40 LargeT, the hTERT and/or the antibiotic resistance transgenes.

* * * * *